(12) United States Patent
Zhao et al.

(10) Patent No.: US 11,948,693 B2
(45) Date of Patent: Apr. 2, 2024

(54) TRADITIONAL CHINESE MEDICINE SYNDROME CLASSIFICATION METHOD BASED ON MULTI-GRAPH ATTENTION

(71) Applicant: Nanjing Dajing TCM Information Technology Co. LTD, Nanjing (CN)

(72) Inventors: Jing Zhao, Nanjing (CN); Wenyou Li, Nanjing (CN); Zhaoyang Jiang, Nanjing (CN); Jie Yin, Nanjing (CN); Ying Chen, Nanjing (CN)

(73) Assignee: NANJING DAJING TCM INFORMATION TECHNOLOGY CO. LTD, Nanjing (CN)

( * ) Notice: Subject to any disclaimer, the term of this patent is extended or adjusted under 35 U.S.C. 154(b) by 0 days.

(21) Appl. No.: 18/337,459

(22) Filed: Jun. 20, 2023

(65) Prior Publication Data

US 2023/0335296 A1  Oct. 19, 2023

(30) Foreign Application Priority Data

Nov. 7, 2022  (CN) .......................... 202211381693.4

(51) Int. Cl.
*G16H 50/70* (2018.01)
*G16H 20/90* (2018.01)

(52) U.S. Cl.
CPC .............. *G16H 50/70* (2018.01); *G16H 20/90* (2018.01)

(58) Field of Classification Search
CPC ...................................................... G16H 50/70
See application file for complete search history.

(56) References Cited

U.S. PATENT DOCUMENTS

| | | | |
|---|---|---|---|
| 11,593,618 B2* | 2/2023 | Itou ........................ | G06N 3/045 |
| 2019/0070236 A1 | 3/2019 | Wang et al. | |
| 2019/0070237 A1 | 3/2019 | Hu et al. | |
| 2019/0070246 A1 | 3/2019 | Ma et al. | |
| 2020/0104409 A1* | 4/2020 | Busbridge ............. | G06F 16/258 |
| 2020/0104729 A1* | 4/2020 | Busbridge ............. | G06N 3/042 |

(Continued)

FOREIGN PATENT DOCUMENTS

| | | | | |
|---|---|---|---|---|
| CN | 115423052 A | * | 12/2022 | ............. G16H 50/70 |
| CN | 115618225 A | * | 1/2023 | |

OTHER PUBLICATIONS

CNIPA, Notification of First Office Action for Chinese application CN202211381693.4, dated Dec. 26, 2022.

(Continued)

*Primary Examiner* — Jay M. Patel
(74) *Attorney, Agent, or Firm* — Zhigang Ma

(57) ABSTRACT

The present disclosure provides a traditional Chinese medicine (TCM) syndrome classification method based on multi-graph attention, which comprehensively considers the contribution of symptoms and syndrome elements in syndrome classification by constructing a graph structure, integrates a symptom-symptom graph and a symptom-syndrome element graph into classification, uses a multi-graph attention network to aggregate the features of symptoms and syndrome elements, and finally realizes syndrome classification through a multi-layer perceptron. At the same time, extensive experiments are carried out on real data sets, the effectiveness of the multi-graph attention network is verified, more accurate classification is realized, and better classification results have been achieved.

7 Claims, 2 Drawing Sheets

(56) References Cited

U.S. PATENT DOCUMENTS

| | | | |
|---|---|---|---|
| 2021/0081717 A1* | 3/2021 | Creed | G06N 5/022 |
| 2021/0233658 A1* | 7/2021 | Van Assel | G16H 70/60 |
| 2022/0092267 A1* | 3/2022 | Hou | G06F 40/279 |
| 2022/0277858 A1* | 9/2022 | Zhao | G06N 3/0442 |
| 2022/0383108 A1* | 12/2022 | Cheng | G06N 3/09 |
| 2022/0383992 A1* | 12/2022 | Triendl | G06N 3/045 |
| 2023/0267302 A1* | 8/2023 | Perozzi | G06N 3/08 |
| | | | 706/25 |

OTHER PUBLICATIONS

CNIPA, Notification to grant patent right for Chinese application CN202211381693.4, dated Jan. 11, 2023.

\* cited by examiner

TRADITIONAL CHINESE MEDICINE SYNDROME CLASSIFICATION METHOD BASED ON MULTI-GRAPH ATTENTION

TECHNICAL FIELD

The present disclosure relates to the technical field of classification, in particular, but not limited to, a traditional Chinese medicine (TCM) syndrome classification method based on multi-graph attention.

BACKGROUND

Traditional Chinese medicine has a long history and profound connotation, which has made great contributions to the health of all mankind. At the same time, in the treatment of patients in COVID-19, Traditional Chinese medicine showed obvious curative effects and played an important role in fighting the epidemic. Syndrome types are different disease states of the human body caused by different changes in yin and yang, qi and blood caused by different causes. The syndrome type can reveal the mechanism and development trend of diseases. Traditional Chinese medicine takes it as the basis for determining treatment and prescribing drugs, so that it is very important to realize accurate classification of syndrome types in the treatment of traditional Chinese medicine.

Doctors judge syndrome types by four diagnostic methods: inspecting, listening, questioning and feeling, based on personal experience, which only relies on personal experience and is highly subjective, so that it is difficult to promote traditional Chinese medicine. With the development of artificial intelligence technology, many algorithms of machine learning and deep learning have been applied to syndrome classification, which combines traditional Chinese medicine with computer-aided diagnosis. As proposed by Zhu Wenfeng et al., in "Application of Bayesian Network in Traditional Chinese Medicine Syndrome Differentiation System", the diagnosis result of Bayesian network combined with relevant experience and an algorithm model is the same as that of experienced old Traditional Chinese medicine practitioners. As proposed by Zhang Chengjiang et al., in "Mining Algorithm of Association Rules in Traditional Chinese Medicine Nephropathy Treatment Information", the classical prior correlation algorithm and the fp-growth correlation algorithm are applied to TCM syndrome classification, and the data mining technology is used to find the mapping relationship between TCM symptoms and TCM syndrome types. As proposed by Wu Liao et al., in "Study of BP Neural Network Based on Conjugate Gradient Descent Algorithm on TCM Diabetes Diagnosis Model", a conjugate gradient algorithm is constructed to establish a BP neural network for treating coronary heart disease syndrome in TCM. The model refers to 14 syndromes and performs well. As proposed by Hu et al., in "A Preliminary Study on Imbalanced Syndrome Differentiation of Cold and Heat", a neural network classifier is used to distinguish cold syndrome and heat syndrome, and the effectiveness of this method is verified through the insensitivity of fastText to unbalanced data.

However, the existing methods only consider the relationship between symptoms and syndrome types, without taking into account the syndrome element which is a key component. At the same time, the relationship between symptoms and syndrome types is very complex and nonlinear, so that it is difficult to accurately extract the relationship between symptoms and syndrome types by using traditional machine learning methods. In this way, the existing algorithm is not accuracy.

In view of this, it is necessary to provide a new method to solve at least some of the above problems.

SUMMARY

Aiming at one or more problems in the prior art, the present disclosure provides a traditional Chinese medicine (TCM) syndrome classification method based on multi-graph attention, which comprehensively considers the contribution of symptoms and syndrome elements in syndrome classification by constructing a graph structure, integrates a symptom-symptom graph and a symptom-syndrome element-symptom graph into classification, uses a multi-graph attention network to aggregate the features of symptoms and syndrome elements, and finally realizes syndrome classification through a multi-layer perceptron. At the same time, extensive experiments are carried out on real data sets, the effectiveness of the multi-graph attention network is verified, more accurate classification is realized, and better classification results have been achieved.

The technical solution to achieve the purpose of the present disclosure is as follows.

A traditional Chinese medicine (TCM) syndrome classification method based on multi-graph attention is provided, comprising:

Step 1, acquiring a data set containing a plurality of clinical data, and constructing a symptom-symptom graph Ss a symptom-syndrome element graph Se and a symptom embedding matrix em by using the relationship between a symptom and a syndrome element;

Step 2, performing graph attention feature aggregation on a symptom-symptom graph Ss and a symptom-syndrome element graph Se based on a multi-graph attention network to obtain a feature representation $H_{i_s}$ between symptoms and symptoms and a feature representation $H_{i_e}$ between symptoms and syndrome elements; performing matrix splicing on the feature representation $H_{i_s}$ between symptoms and symptoms and the feature representation $H_{i_e}$ between symptoms and syndrome elements to obtain a new symptom feature representation $H_i$; multiplying the symptom embedding matrix em with a new symptom feature representation $H_i$ to obtain a symptom combination feature representation H, wherein the symptom combination feature representation H contains information of symptoms and syndrome elements;

Step 3, based on the symptom combination feature representation H, using a multi-layer perceptron MLP as a classifier for syndrome classification and prediction.

Further, according to the TCM syndrome classification method based on multi-graph attention provided by the present disclosure, in Step 1, each clinical data is represented by multi-thermal coding of symptoms, syndrome elements and syndrome types: a symptom set s={$s_1$, $s_2$, $s_3$, ... $s_m$} a syndrome element set se={$se_1$, $se_2$, $se_3$, ... $se_k$} and a syndrome type set sy={$sy_1$, $sy_2$, $sy_3$, ... $sy_l$}, where m is the number of symptoms contained in the data set, k is the number of syndrome elements contained in the data set, and l is the number of syndrome types contained in the data set; for any clinical data, if the i-th symptom/syndrome element/syndrome type appears, the corresponding position in the corresponding symptom set s/syndrome element set se/syndrome type set sy is set as 1, otherwise it is set as 0.

Further, according to the TCM syndrome classification method based on multi-graph attention provided by the present disclosure, the specific step of constructing a symptom-symptom graph, a symptom-syndrome element graph and a symptom embedding matrix in Step 1 comprises:

Step 1-1: constructing a symptom-symptom undirected graph Ss: counting the frequency of all symptoms appearing in clinical data, extracting the symptoms with frequency ≥threshold M, and connecting the symptoms in pairs to form the symptom-symptom undirected graph Ss;

Step 1-2: constructing a symptom-syndrome element undirected graph Se: comparing any two clinical data, counting the number of the same syndrome elements in the two clinical data, and connecting the symptoms of the two clinical data if the number of the same syndrome elements is greater than the threshold N;

Step 1-3: constructing a symptom embedding matrix em={$em_1$, $em_2$, $em_3$, ... $em_n$} and defining $em_i$=s={$s_1$, $s_2$, $s_3$, ... $s_m$}, where n is the total number of clinical data.

Further, according to the TCM syndrome classification method based on multi-graph attention provided by the present disclosure, in Step 2, the specific step of performing graph attention feature aggregation on a symptom-symptom graph Ss and a symptom-syndrome element graph Se based on a multi-graph attention network comprises:

1) calculating an attention coefficient $e_{ij}$ of a node pair (i,j) in the symptom-symptom graph Ss and the symptom-syndrome element graph Se:

$$e_{ij}=\text{LeakyReLU}(\vec{a}^T\,[WH_i\|WH_j]) \quad (1)$$

where $W \in R^{F*F'}$ is a shared weight matrix, F is the number of input features, F' is the number of output features, $H_i$ is the feature of node i, $H_j$ is the feature of node j, $\vec{a}^T$ is the mapping of splicing vectors to real numbers, LeakyReLU is an activation function, and the node pair (i,j) refers to two points with edges connected in an undirected graph;

normalizing the attention coefficient of each node pair (i,j) to obtain a normalized attention coefficient $\alpha_{ij}$:

$$\alpha_{ij} = \frac{\exp(e_{ij})}{\sum_{k\in N_i}\exp(e_{ik})} \quad (2)$$

where $N_i$ is a neighbor node of i;

2) gathering the symptoms of the symptom-symptom graph Ss to a first-order neighboring point to obtain a first-order symptom aggregation representation $H_{i_s}^{1'}$:

$$H_{i_s}^{1'} = \|_{k=1}^{K} \sigma\left(\sum_{j_s\in N_{i_s}} \alpha_{i_s j_s}^k W_s^k H_{j_s}^0\right) \quad (3)$$

where K indicates the number of heads of attention, $N_{i_s}$ is a first-order neighbor of node $i_s$, $\alpha_{i_s j_s}$ is a cross-correlation coefficient of attention of the symptom-symptom graph, $W_s$ is a linear transformation matrix of input features of the symptom-symptom graph, $H_{j_s}^0$ is an original feature representation of adjacent nodes of the symptom-symptom graph, and σ is an ELU activation function;

adding a residual term to the first-order symptom aggregation representation $H_{i_s}^{1'}$ to obtain the feature aggregation result $H_{i_s}^1$ of a first-layer graph attention network of the symptom-symptom graph Ss as follows:

$$H_{i_s}^1 = H_{i_s}^{1'} + \text{Linear}(H_{i_s}^0) \quad (4)$$

where Linear is a linear layer, $H_{i_s}^0$ is a residual term of the symptom-symptom graph in the model;

similarly, the feature aggregation result $H_{i_e}^1$, of the first-layer graph attention network of the symptom-syndrome element graph Se is as follows:

$$H_{i_e}^1 = \|_{k=1}^{K} \sigma\left(\sum_{j_e\in N_{i_e}} \alpha_{i_e j_e}^k W_e^k H_{j_e}^0\right) + \text{Linear}(H_{i_e}^0) \quad (5)$$

where $N_{i_e}$ is a first-order neighbor of the node $i_e$, $\alpha_{i_e j_e}$ is a cross-correlation coefficient of the attention of the symptom-syndrome element graph, $W_e$ is a linear transformation matrix of the input features of the symptom-syndrome element graph, $H_{j_e}^0$ is an original feature representation of the adjacent nodes of the symptom-syndrome element graph, and $H_{i_e}^0$ is a residual term of the symptom-syndrome element graph in the model;

3) by stacking multi-layer graph attention, aggregating the features of high-order adjacent nodes of the symptom-symptom graph Ss and the symptom-syndrome element graph Se, respectively, to obtain the feature aggregation result $H_{i_s}^l$ of the attention network of the lth-layer graph of the symptom-symptom graph Ss as follows:

$$H_{i_s}^l = \|_{k=1}^{K} \sigma\left(\sum_{j_s\in N_{i_s}} \alpha_{i_s j_s}^k W_s^k H_{j_s}^{l-1}\right) + H_{i_s}^{l-1}(1<l<L) \quad (6)$$

where l is the current number of layers, and L is the total number of layers in the graph attention network, in which 1<l<L;

the feature aggregation result $H_{i_e}^l$ of the lth-layer graph attention network of the symptom-syndrome element graph Se is as follows:

$$H_{i_e}^l = \|_{k=1}^{K} \sigma\left(\sum_{j_e\in N_{i_e}} \alpha_{i_e j_e}^k W_e^k H_{j_e}^{l-1}\right) + H_{i_e}^{l-1}(1<l<L) \quad (7)$$

4) if the multi-head attention in the last layer takes the average of all multi-head attentions, obtaining the feature aggregation result $H_{i_s}^L$ of the Lth-layer graph attention network of the symptom-symptom graph Ss as follows:

$$H_{i_s}^L = \sigma\left(\frac{1}{K}\sum_{k=1}^{K}\sum_{j_s\in N_{i_s}} \alpha_{i_s j_s}^k W_s^k H_{j_s}^{L-1}\right) + \text{Linear}(H_{i_s}^{L-1}) \quad (8)$$

the feature aggregation result $H_{i_e}^L$ of the Lth-layer graph attention network of the symptom-syndrome element graph Se is as follows:

$$H_{i_e}^L = \sigma\left(\frac{1}{K}\sum_{k=1}^{K}\sum_{j_e\in N_{i_e}} \alpha_{i_e j_e}^k W_e^k H_{j_e}^{L-1}\right) + \text{Linear}(H_{i_e}^{L-1}) \quad (9)$$

the feature aggregation result $H_{i_s}^L$ of the Lth-layer graph attention network of the symptom-symptom graph Ss is the feature representation $H_{i_s}$ between symptoms and symptoms, and the feature aggregation result $H_{i_e}^L$ of the Lth-layer graph attention network of the symptom-syndrome element graph Se is the feature representation between symptoms and symptom elements.

Further, according to the TCM syndrome classification method based on multi-graph attention provided by the present disclosure, the formula of matrix splicing operation in Step 2 is as follows:

$$H_i = Cat(H_{i_s}, H_{i_e}) \qquad (10)$$

where Cat is the splicing operation of two matrices.

Further, according to the TCM syndrome classification method based on multi-graph attention provided by the present disclosure, the symptom combination feature representation H is as follows:

$$H = MUL(em, H_i) \qquad (11)$$

where MUL is the multiplication operation of two matrices.

Further, according to the TCM syndrome classification method based on multi-graph attention provided by the present disclosure, the specific step of using a multi-layer perceptron MLP for syndrome classification and prediction comprises:

inputting the symptom combination feature representation H into the multi-layer perceptron MLP, and obtaining the category of the syndrome type $y_s$ predicted by the model after calculation:

$$y_s = sigmoid(W_2(W_1 * H + b_1) + b_2) \qquad (12)$$

where $W_1$ and $W_2$ are the weight matrix of the first layer and the second layer, respectively, $b_1$ and $b_2$ are the offset vectors of the first layer and the second layer, respectively, and the category with the highest probability is the result of classification;

using the BCE loss function to calculate the difference L between the model prediction and the actual output used to train the model;

$$L = -\frac{1}{n}\sum_{s=1}^{n}[t_s \log(y_s) + (1 - t_s) \log(1 - y_s)] \qquad (13)$$

where n is the number of categories of the syndrome type, and $t_s$ is a real category.

A traditional Chinese medicine (TCM) syndrome classification system based on multi-graph attention and a multi-layer perceptron is provided, comprising:

a multi-graph constructing module, which constructs a symptom-symptom graph, a symptom-syndrome element graph and a symptom embedding matrix by using the relationship between a symptom and a syndrome element based on a clinical data set;

a multi-graph attention feature aggregating module, which performs graph attention feature aggregation on the symptom-symptom graph Ss and the symptom-syndrome element graph Se based on a multi-graph attention network and performs matrix splicing to obtain a new symptom feature representation; and multiplies the symptom embedding matrix with the new symptom feature representation to obtain a symptom combination feature representation;

a syndrome classifying module, which uses a multi-layer perceptron as a classifier for syndrome classification and prediction based on the symptom combination feature representation.

Compared with the prior art, the present disclosure has the following technical effects.

1. The TCM syndrome classification method based on multi-graph attention of the present disclosure uses a plurality of undirected graphs to construct a multi-graph attention network (MGAT) model, and obtains a more expressive symptom comprehensive embedding representation.

2. The TCM syndrome classification method based on multi-graph attention according to the present disclosure introduces the relationship between symptoms and syndrome elements of a plurality of graphs, and uses a multi-graph attention network to obtain a new feature representation containing information of symptoms and syndrome elements.

3. The multi-graph attention network (MGAT) model constructed in the TCM syndrome classification method based on multi-graph attention according to the present disclosure not only conforms to the theory of TCM, but also shows outstanding performance in syndrome classification. Experiments are carried out on the data set of febrile diseases widely used in the field of TCM, and the advantages of the classification method according to the present disclosure are verified.

BRIEF DESCRIPTION OF THE DRAWINGS

The accompanying drawings are used to provide a further understanding of the present disclosure, and together with the description, serve to explain the embodiments of the present disclosure, rather than limit the present disclosure. In the figures.

DETAILED DESCRIPTION OF THE EMBODIMENTS

In order to further understand the present disclosure, the preferred embodiments of the present disclosure are described with reference to the examples hereinafter, but it should be understood that these descriptions are only for further explaining the features and advantages of the present disclosure, rather than limit the claims of the present disclosure.

The description of this part is only for typical embodiments, and the present disclosure is not limited to the scope described by the embodiments. The combination of different embodiments and some technical features in different embodiments are mutually substituted. The same or similar prior art means and some technical features in embodiments are mutually substituted, which also falls within the scope of description and protection of the present disclosure.

Because a single symptom graph can only aggregate a part of the information, the graph attention network cannot represent the relationship between symptoms and syndrome elements well. The present disclosure provides a multi-graph attention network (MGAT) by integrating a symptom-symptom graph and a symptom-syndrome element-symptom graph into classification.

Figure 1:
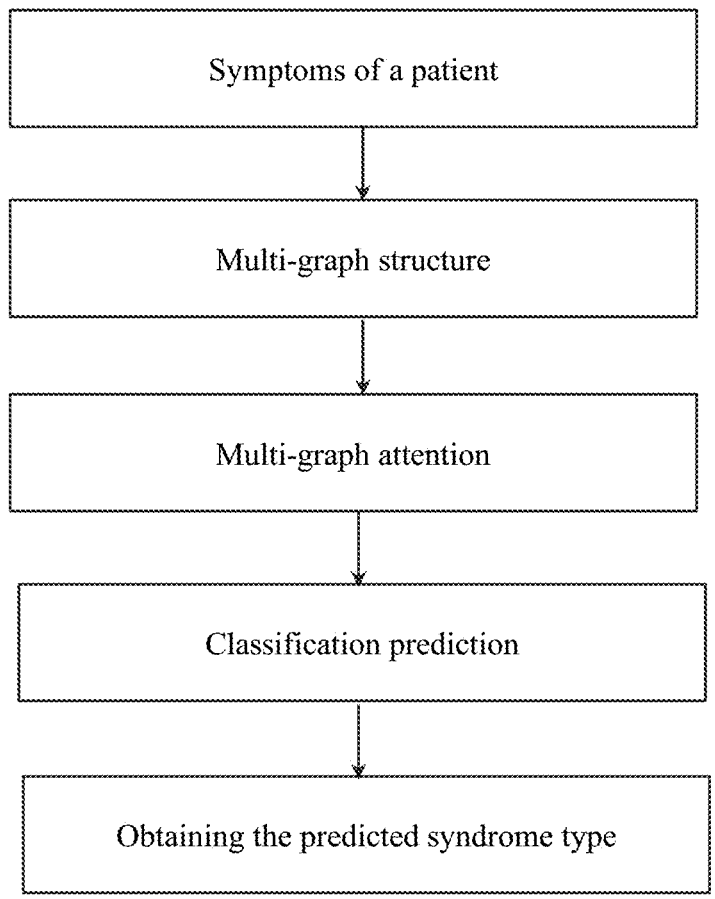
FIG. 1 shows a flow chart of a TCM syndrome classification method based on multi-graph attention according to the present disclosure.

According to one aspect of the present disclosure, a TCM syndrome classification method based on multi-graph attention, as shown in FIG. 1, comprises the following steps.

Step 1, a data set containing a plurality of clinical data is acquired, and a symptom-symptom graph Ss, a symptom-syndrome element graph Se and a symptom embedding matrix em are constructed by using the relationship between a symptom and a syndrome element. The specific step comprises:

Step 1-1: constructing a symptom-symptom undirected graph Ss: counting the frequency of all symptoms appearing in clinical data, extracting the symptoms with frequency≥threshold M, and connecting the symptoms in pairs to form the symptom-symptom undirected graph Ss;

Step 1-2: constructing a symptom-syndrome element undirected graph Se: comparing any two clinical data, counting the number of the same syndrome elements in the two clinical data, and connecting the symptoms of the two clinical data if the number of the same syndrome elements is greater than the threshold N, in which if two symptoms and a plurality of syndromes coexist, there is a special relationship between the two symptoms, which is the basis for constructing the symptom-syndrome element undirected graph;

Step 1-3: constructing a symptom embedding matrix em={em$_1$, em$_2$, em$_3$, ... em$_n$} and defining em$_i$=s={s$_1$, s$_2$, s$_3$, ... s$_m$}, where n is the total number of clinical data.

Preferably, each clinical data is represented by multi-thermal coding of symptoms, syndrome elements and syndrome types: a symptom set s={s$_1$, s$_2$, s$_3$, ... s$_m$}, a syndrome element set se={se$_1$, se$_2$, se$_3$, ... se$_k$} and a syndrome type set sy={sy$_1$, sy$_2$, sy$_3$, ... sy$_l$}, where m is the number of symptoms contained in the data set, k is the number of syndrome elements contained in the data set, and l is the number of syndrome types contained in the data set; for any clinical data, if the i-th symptom/syndrome element/syndrome type appears, the corresponding position in the corresponding symptom set s/syndrome element set se/syndrome type set sy is set as 1, otherwise it is set as 0.

Step 2, graph attention feature aggregation is performed on a symptom-symptom graph Ss and a symptom-syndrome element graph Se based on a multi-graph attention network to obtain a feature representation $H_{i_s}$ between symptoms and symptoms and a feature representation $H_{i_e}$ between symptoms and syndrome elements. The specific step comprises:

1) calculating an attention coefficient $e_{ij}$ of a node pair (i,j) in the symptom-symptom graph Ss and the symptom-syndrome element graph Se:

$$e_{ij} = \text{LeakyReLU}(\vec{a}^T [WH_i \| WH_j]) \quad (1)$$

where $W \in R^{F*F'}$ is a shared weight matrix, F is the number of input features, F' is the number of output features, $H_i$ is the feature of node i, $H_j$ is the feature of node j, $\vec{a}^T$ is the mapping of splicing vectors to real numbers, LeakyReLU is an activation function, and the node pair (i,j) refers to two points with edges connected in an undirected graph;

normalizing the attention coefficient of each node pair (i,j) to obtain a normalized attention coefficient $\alpha_{ij}$:

$$\alpha_{ij} = \frac{\exp(e_{ij})}{\sum_{k \in N_i} \exp(e_{ik})} \quad (2)$$

where $N_i$ is a neighbor node of i;

2) gathering the symptoms of the symptom-symptom graph Ss to a first-order neighboring point to obtain a first-order symptom aggregation representation $H_{i_s}^{1'}$:

$$H_{i_s}^{1'} = \|_{k=1}^{K} \sigma \left( \sum_{j_s \in N_{i_s}} \alpha_{i_s j_s}^k W_s^k H_{j_s}^0 \right) \quad (3)$$

where K indicates the number of heads of attention, $N_{i_s}$ is a first-order neighbor of node $i_s$, $\alpha_{i_s j_s}$ is a cross-correlation coefficient of attention of the symptom-symptom graph, $W_s$ is a linear transformation matrix of input features of the symptom-symptom graph, $H_{j_s}^0$ is an original feature representation of adjacent nodes of the symptom-symptom graph, and $\sigma$ is an ELU activation function;

adding a residual term to the first-order symptom aggregation representation $H_{i_s}^{1'}$ to obtain the feature aggregation result $H_{i_s}^1$ of a first-layer graph attention network of the symptom-symptom graph Ss as follows:

$$H_{i_s}^1 = H_{i_s}^{1'} + \text{Linear}(H_{i_s}^0) \quad (4)$$

where Linear is a linear layer, $H_{i_s}^0$ is a residual term of the symptom-symptom graph in the model;

similarly, the feature aggregation result $H_{i_e}^1$ of the first-layer graph attention network of the symptom-syndrome element graph Se is as follows:

$$H_{i_e}^1 = \|_{k=1}^{K} \sigma \left( \sum_{j_e \in N_{i_e}} \alpha_{i_e j_e}^k W_e^k H_{j_e}^0 \right) + \text{Linear}(H_{i_e}^0) \quad (5)$$

where $N_{i_e}$ is a first-order neighbor of the node $i_e$, $\alpha_{i_e j_e}$ is a cross-correlation coefficient of the attention of the symptom-syndrome element graph, $W_e$ is a linear transformation matrix of the input features of the symptom-syndrome element graph, $H_{j_e}^0$ is an original feature representation of the adjacent nodes of the symptom-syndrome element graph, and $H_{i_e}^0$ is a residual term of the symptom-syndrome element graph in the model;

3) by stacking multi-layer graph attention, aggregating the features of high-order adjacent nodes of the symptom-symptom graph Ss and the symptom-syndrome element graph Se, respectively, to obtain the feature aggregation result $H_{i_s}^l$ of the attention network of the lth-layer graph of the symptom-symptom graph Ss as follows:

$$H_{i_s}^l = \|_{k=1}^{K} \sigma \left( \sum_{j_s \in N_{i_s}} \alpha_{i_s j_s}^k W_s^k H_{j_s}^{l-1} \right) + H_{i_s}^{l-1} (1 < l < L) \quad (6)$$

where l is the current number of layers, and L is the total number of layers in the graph attention network;

the feature aggregation result $H_{i_e}^l$ of the lth-layer graph attention network of the symptom-syndrome element graph Se is as follows:

$$H_{i_e}^l = \prod_{k=1}^{K} \sigma\left(\sum_{j_e \in N_{i_e}} \alpha_{i_e j_e}^k W_e^k H_{j_e}^{l-1}\right) + H_{i_e}^{l-1}(1 < l < L) \quad (7)$$

4) if the multi-head attention in the last layer takes the average of all multi-head attentions, obtaining the feature aggregation result $H_{i_s}^L$ the Lth-layer graph attention network of the symptom-symptom graph Ss as follows:

$$H_{i_s}^L = \sigma\left(\frac{1}{K}\sum_{k=1}^{K} \sum_{j_s \in N_{i_s}} \alpha_{i_s j_s}^k W_s^k H_{j_s}^{l-1}\right) + \text{Linear}\left(H_{i_s}^{L-1}\right) \quad (8)$$

the feature aggregation result $H_{i_e}^L$ the Lth-layer graph attention network of the symptom-syndrome element graph Se is as follows:

$$H_{i_e}^L = \sigma\left(\frac{1}{K}\sum_{k=1}^{K} \sum_{j_e \in N_{i_e}} \alpha_{i_e j_e}^k W_e^k H_{j_e}^{L-1}\right) + \text{Linear}\left(H_{i_e}^{L-1}\right) \quad (9)$$

the feature aggregation result of the Lth-layer graph attention network of the symptom-symptom graph Ss is the feature representation $H_{i_s}$ between symptoms and symptoms, and the feature aggregation result $H_{i_e}^L$ of the Lth-layer graph attention network of the symptom-syndrome element graph Se is the feature representation $H_{i_e}$ between symptoms and symptom elements.

matrix splicing is performed on the feature representation $H_{i_s}$ between symptoms and symptoms and the feature representation $H_{i_e}$ between symptoms and symptom elements to obtain a new symptom feature representation $H_i$; the formula of matrix splicing operation is as follows:

$$H_i = Cat(H_{i_s}, H_{i_e}) \quad (10)$$

where Cat is the splicing operation of two matrices;

multiplying the symptom embedding matrix em with the new symptom feature representation $H_i$ to obtain a symptom combination feature representation H, wherein the symptom combination feature representation H contains information of symptoms and syndrome elements. The symptom combination feature representation H is as follows:

$$H = MUL(em, H_i) \quad (11)$$

where MUL is the multiplication operation of two matrices;

Step 3, based on the symptom combination feature representation H, a multi-layer perceptron MLP is used as a classifier for syndrome classification and prediction. The specific step comprises:

inputting the symptom combination feature representation H into the multi-layer perceptron MLP, and obtaining the category of the syndrome type $y_s$ predicted by the model after calculation:

$$y_s = \text{sigmoid}(W_2(W_1 * H + b_1) + b_2) \quad (12)$$

where $W_1$ and $W_2$ are the weight matrix of the first layer and the second layer, respectively, $b_1$ and $b_2$ are the offset vectors of the first layer and the second layer, respectively, and the category with the highest probability is the result of classification;

using the BCE loss function to calculate the difference L between the model prediction and the actual output used to train the model;

$$L = -\frac{1}{n}\sum_{s=1}^{n}[t_s \log(y_s) + (1 - t_s)\log(1 - y_s)] \quad (13)$$

where n is the number of categories of the syndrome type, and $t_s$ is a real category.

Figure 2:
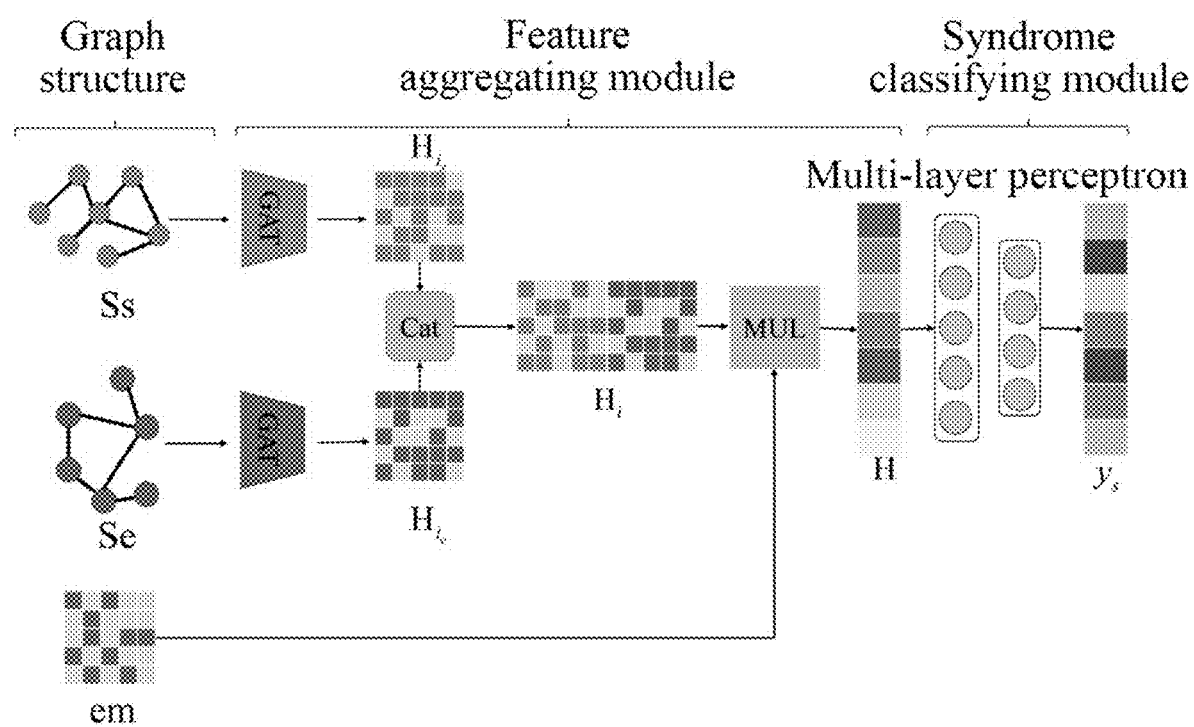
FIG. 2 shows a schematic diagram of a multi-graph attention network model of a TCM syndrome classification method based on multi-graph attention according to the present disclosure.

According to another present disclosure of the present disclosure, a traditional Chinese medicine (TCM) syndrome classification system based on multi-graph attention and a multi-layer perceptron, as shown in FIG. 2, comprises:

a multi-graph constructing module, which constructs a symptom-symptom graph, a symptom-syndrome element graph and a symptom embedding matrix by using the relationship between a symptom and a syndrome element based on a clinical data set;

a multi-graph attention feature aggregating module, which performs graph attention feature aggregation on the symptom-symptom graph Ss and the symptom-syndrome element graph Se based on a multi-graph attention network and performs matrix splicing to obtain a new symptom feature representation; and multiplies the symptom embedding matrix with the new symptom feature representation to obtain a symptom combination feature representation;

a syndrome classifying module, which uses a multi-layer perceptron as a classifier for syndrome classification and prediction based on the symptom combination feature representation.

Embodiment 1

A traditional Chinese medicine (TCM) syndrome classification method based on multi-graph attention is provided, comprises the following modules.

(1) Multi-Graph Structure

In the data set, each clinical data can be represented by multi-thermal coding of symptoms, syndrome elements and syndrome types: $s=\{s_1, s_2, s_3, \ldots s_m\}$, $se=\{se_1, se_2, se_3, \ldots se_k\}$ and $sy=\{sy_1, sy_2, sy_3, \ldots sy_t\}$. If the i-th symptom appears, the corresponding position $s_i$ in the symptom set s is set as 1, otherwise it is set as 0. Similarly, the syndrome element set se and the syndrome set sy can also be expressed in this way.

The two constructed undirected graphs are then defined, namely, a symptom-symptom graph Ss and a symptom-syndrome element graph Se. The construction rule of the symptom-symptom graph Ss is to count the frequency of all symptoms appearing in clinical data, extract the symptoms with frequency greater than or equal to threshold M, and connect the symptoms to form a graph. The construction rule of the symptom-syndrome element graph Se is to compare the same number of syndromes in two clinical data. If the number of the same syndrome elements is greater than the threshold N, the symptoms of the two data are connected to each other to form a graph. If two symptoms and a plurality of syndromes coexist, there is a special relationship between the two symptoms, A symptom embedding matrix is $em=\{em_1, em_2, em_3, \ldots em_n\}$, where n is the total number of clinical data. $em_i = s = \{s_1, s_2, s_3, \ldots s_m\}$ is then defined, where m is the number of symptoms contained in the data set. If symptom $S_1$ appears in clinical data, it is set as 1, otherwise it is set as 0.

(2) Multi-Graph Attention Feature Aggregating Module

In the module, the symptom-symptom graph Ss and the symptom-syndrome element graph Se are input into different GAT modules for calculation, respectively, and the new symptom feature representations $H_{i_s}$ and $H_{i_e}$ are obtained, wherein $H_{i_s}$ integrates the features between symptoms and symptoms, and $H_{i_e}$ integrates the features between symptoms and syndrome elements. Then, $H_{i_s}$ and $H_{i_e}$ are merged to obtain a new symptom feature representation $H_i$. Finally, the symptom embedding matrix em is multiplied by $H_i$ to obtain the symptom combination feature representation H.

First, the calculation of the attention coefficient is introduced. The attention value $e_{ij}$ between the node pair (i,j) formed by any two points with edges connected in the symptom-symptom graph Ss and the symptom-syndrome element graph Se:

$$e_{ij} = \text{LeakyReLU}(\vec{a}^T [WH_i \| WH_j]) \quad (1)$$

where $W \in R^{F*F'}$ is a shared weight matrix, F is the number of input features, F' is the number of output features, $H_i$ is the feature of node i, $H_j$ is the feature of node j, and $\vec{a}^T$ is the mapping of splicing vectors to real numbers, which is activated by LeakyReLU.

When aggregating neighbor information, the attention coefficient of each node pair needs to be normalized to obtain $\alpha_{ij}$:

$$\alpha_{ij} = \frac{\exp(e_{ij})}{\sum_{k \in N_i} \exp(e_{ik})} \quad (2)$$

where $N_i$ is a neighbor node of i.

For the symptom-symptom graph Ss, the process of gathering symptoms to the first-order neighboring point is defined as:

$$H_{i_s}^{1'} = \prod_{k=1}^{K} \sigma \left( \sum_{j_s \in N_{i_s}} \alpha_{i_s j_s}^k W_s^k H_{j_s}^0 \right) \quad (3)$$

where K indicates the number of heads of attention, $N_{i_s}$ is a first-order neighbor of node $i_s$, $\alpha_{i_s j_s}$ is a cross-correlation coefficient of attention of the symptom-symptom graph, $W_s$ is a linear transformation matrix of input features, $H_{j_s}^0$ an original feature representation of adjacent nodes, and $\sigma$ is an ELU activation function.

In order to avoid the problem of gradient disappearance caused by too deep layers, the residual term is added to this model, and the result obtained after the first layer of GAT is as follows:

$$H_{i_s}^1 = H_{i_s}^{1'} + \text{Linear}(H_{i_s}^0) \quad (4)$$

where $H_{i_s}^{1'}$ is a first-order symptom aggregation representation, and Linear is a linear layer. $H_{i_s}^0$ and $H_{i_s}^{1'}$ cannot be directly added because they different in dimension.

Similarly, the node aggregation process for the symptom-syndrome element graph Se can be defined as:

$$H_{i_e}^1 = \prod_{k=1}^{K} \sigma \left( \sum_{j_e \in N_{i_e}} \alpha_{i_e j_e}^k W_e^k H_{j_e}^0 \right) + \text{Linear}(H_{i_e}^0) \quad (5)$$

where $N_{i_e}$ is a first-order neighbor of the node $i_e$, $\alpha_{i_e j_e}$ is a cross-correlation coefficient of the attention, $W_e$ is a linear transformation matrix of the input features, and $H_{j_e}^0$ is an original feature representation of the adjacent nodes.

The above content is only the graph attention feature aggregation on one layer, which can be extended to multi-layer feature aggregation. For the feature aggregation of the lth-layer, the aggregation process is defined as:

$$H_{i_s}^l = \prod_{k=1}^{K} \sigma \left( \sum_{j_s \in N_{i_s}} \alpha_{i_s j_s}^k W_s^k H_{j_s}^{l-1} \right) + H_{i_s}^{l-1} (1 < l < L) \quad (6)$$

$$H_{i_e}^l = \prod_{k=1}^{K} \sigma \left( \sum_{j_e \in N_{i_e}} \alpha_{i_e j_e}^k W_e^k H_{j_e}^{l-1} \right) + H_{i_e}^{l-1} (1 < l < L) \quad (7)$$

where l is the current number of layers, and L is the number of layers of the GAT module. The features of high-order neighboring nodes are aggregated by stacking the multi-layer graph attention.

The graph attention of the last layer is different from the definition of the previous layers, and the multi-head attention of the last layer takes the average of all multi-head attentions:

$$H_{i_s}^L = \sigma \left( \frac{1}{K} \sum_{k=1}^{K} \sum_{j_s \in N_{i_s}} \alpha_{i_s j_s}^k W_s^k H_{j_s}^{L-1} \right) + \text{Linear}(H_{i_s}^{L-1}) \quad (8)$$

$$H_{i_e}^L = \sigma \left( \frac{1}{K} \sum_{k=1}^{K} \sum_{j_e \in N_{i_e}} \alpha_{i_e j_e}^k W_e^k H_{j_e}^{L-1} \right) + \text{Linear}(H_{i_e}^{L-1}) \quad (9)$$

Then, matrix splicing operation is performed on the two obtained new symptom feature representations:

$$H_i = \text{Cat}(H_{i_s}, H_{i_e}) \quad (10)$$

where Cat is the splicing operation of two matrices.

Finally, the symptom embedding matrix em is multiplied with $H_i$ to obtain the symptom combination feature representation H. In other words, this step is the aggregation from a single symptom to a group of symptoms, which is specifically defined as follows:

$$H = \text{MUL}(em, H_i) \quad (11)$$

where MUL is the multiplication operation of two matrices.

(3) Syndrome Classifying Module

The new symptom combination feature representation H contains the information of symptoms and syndrome elements. In the syndrome classifying module, H is used as the input of the MLP, a group of probability values are obtained after calculation, and the category with the highest probability is the classification result. The specific steps are as follows:

$$y_s = \text{sigmoid}(W_2(W_1 * H + b_1) + b_2) \quad (12)$$

where $W_1$ and $W_2$ are the weight matrix of the first layer and the second layer, respectively, and $b_1$ and $b_2$ are the offset vectors of the first layer and the second layer, respectively. $y_s$ is the probability vector of the predicted syndrome type.

Finally, the BCE loss function is used in network training to calculate the difference between the model prediction and the actual output used to train the model:

$$L = -\frac{1}{n}\sum_{s=1}^{n}[t_s \log(y_s) + (1 - t_s)\log(1 - y_s)] \quad (13)$$

where n is the number of categories of the syndrome type, $y_s$ is the category predicted by the model, and $t_s$ is a real category.

Next, the method of this embodiment is verified and evaluated by using an experimental data set.

1) An Experimental Data Set and an Evaluation Index

This experiment is carried out in Python3.9 environment using Pytorch1.10 deep learning library. An experimental device includes an Intel Core i5-11400H processor, NVIDIA GeForce RTX 3050 graphics card and Windows S11 operating system.

In order to verify the effectiveness of the method of the present disclosure, experiments are carried out with real traditional Chinese medicine data sets.

Data Set of Treatise on Febrile Diseases: the data set is compiled from Treatise on Febrile Diseases, a classic work of traditional Chinese medicine. The processed data set contains 173 data, including 697 symptoms, 925 syndrome elements and 173 syndrome types. In this experiment, the ratio of training sets to test sets is 9:1.

In this embodiment, four commonly used indexes are used for evaluation: Accuracy, Precision, Recall and F1-score. Accuracy represents the proportion of samples correctly classified by the syndrome classification algorithm in the total samples. Precision represents the proportion of correct prediction by the algorithm. Recall represents the proportion of true label syndrome types correctly predicted by the algorithm. F1-score is the weighted average of precision and recall. These four evaluation indexes are all positively correlated, and the larger the value, the better the model performance. These indexes are defined as follows:

$$\text{Accuracy} = \frac{TP + TN}{TP + TN + FP + FN} \quad (14)$$

$$\text{Precision} = \frac{TP}{TP + FP} \quad (15)$$

$$\text{Recall} = \frac{TP}{TP + FN} \quad (16)$$

$$F1 - \text{score} = 2g\frac{Precisiong Recall}{Precision + Recall} \quad (17)$$

where TP indicates the number of positive samples correctly predicted, and TN indicates the number of negative samples correctly predicted. FP is the number of negative samples with positive prediction, and FN is the number of positive samples with negative prediction.

2) A Baseline

In this embodiment, the following methods are used to carry out comparative experiments.

Support vector machine (SVM): SVM is a set of related supervised learning methods for classification and regression. The syndrome classification model is established by the SVM, and the best hyperplane is found to realize classification[11].

MLP: the MLP syndrome classification model has two hidden layers. The dimension of the input layer is the number of symptom features, and the dimension of the output layer is the number of categories of syndrome types, which is used to predict the syndrome type[12].

CNN: a convolutional neural network classification model consists of a convolution layer and a fully connected layer. The convolution layer is used to extract symptom features, and the fully connected layer realizes classification. This model realizes relatively accurate classification[13].

GCN: a graph convolution neural network model can better represent the relationship between features. The model consists of a GCN layer and a fully connected layer. The input of the GCN layer is a graph of the relationship between symptoms and symptoms, and the output dimension of the last fully connected layer is the number of categories of syndrome types, which is used to predict the syndrome type.

3) Experimental Results

In order to minimize the influence of randomness on the experimental results, all the experimental results in this embodiment are shown as the average results of 50 runs.

a) Quantitative Analysis

Table 1 shows the comparison between the experimental results of the MGAT and the other four algorithms. The MGAT is superior to the other four algorithms in the evaluation indexes of accuracy, precision, recall and F1-score. Specifically, the MGAT has the accuracy of 82.11%, the precision of 74.18%, the recall of 81.73%, and the F1 score of 76.51%. In addition, the experimental results show that the GCN has the best performance among other comparison algorithms. The MGAT is 7.29%, 4.31%, 8.84% and 5.69% higher than GCN in accuracy, precision, recall and F1-score, respectively. The quantitative experiment shows that the MGAT of the present disclosure significantly improves the accuracy of TCM syndrome classification.

TABLE 1

Experimental results of different methods

| algorithm | Accuracy | Precision | Recall | F1_score |
|---|---|---|---|---|
| SVM | 0.6759 | 0.5980 | 0.6460 | 0.6124 |
| MLP | 0.6833 | 0.5366 | 0.6228 | 0.5638 |
| CNN | 0.7129 | 0.6009 | 0.6877 | 0.6283 |
| GCN | 0.7482 | 0.6987 | 0.7289 | 0.7082 |
| MGAT | 0.8211 | 0.7418 | 0.8173 | 0.7651 | b) Qualitative Analysis

Table 2 shows the comparison between the classification results of the MGAT and the real labels. It can be seen that the first two syndrome types are correctly predicted, and the last syndrome type wrongly predicts the light syndrome of Yangming heat syndrome as the heavy syndrome of Yangming heat syndrome. Because the syndrome elements of the light syndrome of Yangming heat syndrome mainly comprise heat, dry stool, stomach and intestine, which are very similar to the syndrome elements of the heavy syndrome of Yangming heat syndrome, the prediction is wrong. These results show that the MGAT can provide a more accurate syndrome classification model and has a practical value.

TABLE 2

Case analysis

| symptoms | syndrome elements | real labels | MGAT results |
|---|---|---|---|
| Cold hands and feet, weight, sweating, delirium, poor speech | stomach, hot, cold | Yangming heat syndrome | Yangming heat syndrome |
| Delirium, no stool, dull body, restless hands and feet | Heat, poison, yin deficiency, body fluid deficiency, mind, skin | vigorous heat at qi-blood phase | vigorous heat at qi-blood phase |
| Delirium, hot flashes, sweating, dry stool | Heat, dry stool, stomach, intestines, mind | light syndrome of Yangming heat syndrome | heavy syndrome of Yangming heat syndrome |

The TCM syndrome classification method based on multi-graph attention provided by the present disclosure provides a more accurate syndrome classification model and has a practical value, which can significantly improve the accuracy of TCM syndrome classification.

The description and application of the present disclosure here are illustrative, and it is not intended to limit the scope of the present disclosure to the above-mentioned embodiments. The related descriptions of effects or advantages involved in the specification may not be reflected in the actual experimental examples due to the uncertainty of specific conditions and parameters or other factors, and the related descriptions of effects or advantages are not used to limit the scope of the present disclosure. Modifications and variations of the embodiments disclosed herein are possible. Substitutions and equivalent components of the embodiments are well known to those skilled in the art. It should be clear to those skilled in the art that the present disclosure can be implemented in other forms, structures, arrangements, proportions and with other components, materials and elements without departing from the spirit or essential features of the present disclosure. Other modifications and variations can be made to the embodiment disclosed herein without departing from the scope and spirit of the present disclosure.

What is claimed is:

1. A traditional Chinese medicine (TCM) syndrome classification method based on multi-graph attention, comprising:

Step 1, acquiring a data set containing a plurality of clinical data, and constructing a symptom-symptom graph Ss, a symptom-syndrome element graph Se and a symptom embedding matrix em by using the relationship between a symptom and a syndrome element;

Step 2, performing graph attention feature aggregation on a symptom-symptom graph Ss and a symptom-syndrome element graph Se based on a multi-graph attention network to obtain a feature representation $H_{i_s}$ between symptoms and symptoms and a feature representation $H_{i_e}$ between symptoms and syndrome elements; performing matrix splicing on the feature representation $H_{i_s}$ between symptoms and symptoms and the feature representation $H_{i_e}$ between symptoms and syndrome elements to obtain a new symptom feature representation $H_i$; multiplying the symptom embedding matrix em with a new symptom feature representation $H_i$ to obtain a symptom combination feature representation H, wherein the symptom combination feature representation H contains information of symptoms and syndrome elements; wherein the step of performing graph attention feature aggregation on a symptom-symptom graph Ss and a symptom-syndrome element graph Se based on a multi-graph attention network comprises:

1) Calculating an attention coefficient $e_{ij}$ g of a node pair (i,j) in the symptom-symptom graph Ss and the symptom-syndrome element graph Se:

$$e_{ij} = \text{Leaky } ReLU(\vec{a}^T[WH_i \| WH_j]) \quad (1)$$

where $W \in R^{F*F'}$ is a shared weight matrix, F is the number of input features, F' is the number of output features, $H_i$ is the feature of node i, $H_j$ is the feature of node j, $\vec{a}^T$ a is the mapping of splicing vectors to real numbers, LeakyReLU is an activation function, and the node pair (i,j) refers to two points with edges connected in an undirected graph;

normalizing the attention coefficient of each node pair (i,j) to obtain a normalized attention coefficient $\alpha_{ij}$:

$$\alpha_{ij} = \frac{\exp(e_{ij})}{\sum_{k \in N_i} \exp(e_{ik})} \quad (2)$$

where is a neighbor node of i;

2) Gathering the symptoms of the symptom-symptom graph Ss to a first-order neighboring point to obtain a first-order symptom aggregation representation $H_{i_s}^{1'}$:

$$H_{i_s}^{1'} = \|_{k=1}^{K} \sigma\left(\sum_{j_s \in N_{i_s}} \alpha_{i_s j_s}^k W_s^k H_{j_s}^0\right) \quad (3)$$

where K indicates the number of heads of attention, $N_{i_s}$ is a first-order neighbor of node $i_s$, $\alpha_{i_s j_s}$ is a cross-correlation coefficient of attention of the symptom-symptom graph, $W_s$ is a linear transformation matrix of input features of the symptom-symptom graph, $H_{j_s}^0$ is an original feature representation of adjacent nodes of the symptom-symptom graph, and σ is an ELU activation function;

adding a residual term to the first-order symptom aggregation representation $H_{i_s}^{1'}$ to obtain the feature aggregation result $H_{i_s}^{1}$ of a first-layer graph attention network of the symptom-symptom graph Ss as follows:

$$H_{i_s}^{1} = H_{i_s}^{1'} + \text{Linear}(H_{i_s}^{0}) \quad (4)$$

where Linear is a linear layer, $H_{i_s}^{0}$ is a residual term of the symptom-symptom graph in the model;

similarly, the feature aggregation result $H_{i_e}^1$ of the first-layer graph attention network of the symptom-syndrome element graph Se is as follows:

$$H_{i_e}^1 = \overset{K}{\underset{k=1}{\|}} \sigma\left(\sum_{j_e \in N_{i_e}} \alpha_{i_e j_e}^k W_e^k H_{j_e}^0\right) + \text{Linear}(H_{i_e}^0) \quad (5)$$

where $N_{i_e}$ is a first-order neighbor of the node $i_e$, $\alpha_{i_e j_e}$ is a cross-correlation coefficient of the attention of the symptom-syndrome element graph, $W_e$ is a linear transformation matrix of the input features of the symptom-syndrome element graph, $H_{j_e}^0$ is an original feature representation of the adjacent nodes of the symptom-syndrome element graph, and $H_{i_e}^0$ is a residual term of the symptom-syndrome element graph in the model;

3) By stacking multi-layer graph attention, aggregating the features of high-order adjacent nodes of the symptom-symptom graph Ss and the symptom-syndrome element graph Se, respectively, to obtain the feature aggregation result $H_{i_s}^l$ of the attention network of the lth-layer graph of the symptom-symptom graph Ss as follows:

$$H_{i_s}^l = \overset{K}{\underset{k=1}{\|}} \sigma\left(\sum_{j_s \in N_{i_s}} \alpha_{i_s j_s}^k W_s^k H_{j_s}^{l-1}\right) + H_{i_s}^{l-1} (1 < l < L) \quad (6)$$

where l is the current number of layers, and L is the total number of layers in the graph attention network, in which 1<l<L;

the feature aggregation result $H_{i_e}^l$ of the lth-layer graph attention network of the symptom-syndrome element graph Se is as follows:

$$H_{i_e}^l = \overset{K}{\underset{k=1}{\|}} \sigma\left(\sum_{j_e \in N_{i_e}} \alpha_{i_e j_e}^k W_e^k H_{j_e}^{l-1}\right) + H_{i_e}^{l-1} (1 < l < L) \quad (7)$$

4) if the multi-head attention in the last layer takes the average of all multi-head attentions, obtaining the feature aggregation result $H_{i_s}^L$ of the Lth-layer graph attention network of the symptom-symptom graph Ss as follows:

$$H_{i_s}^L = \sigma\left(\frac{1}{K}\sum_{k=1}^K \sum_{j_s \in N_{i_s}} \alpha_{i_s j_s}^k W_s^k H_{j_s}^{L-1}\right) + \text{Linear}(H_{i_s}^{L-1}) \quad (8)$$

the feature aggregation result $H_{i_e}^L$ of the Lth-layer attention network of the symptom-syndrome element graph Se is as follows:

$$H_{i_e}^L = \sigma\left(\frac{1}{K}\sum_{k=1}^K \sum_{j_e \in N_{i_e}} \alpha_{i_e j_e}^k W_e^k H_{j_e}^{L-1}\right) + \text{Linear}(H_{i_e}^{L-1}) \quad (9)$$

the feature aggregation result $H_{i_s}^L$ of the Lth-layer graph attention network of the symptom-symptom graph Ss is the feature representation $H_{i_s}$ between symptoms and symptoms, and the feature aggregation result $H_{i_e}^L$ of the Lth-layer graph attention network of the symptom-syndrome element graph Se is the feature representation $H_{i_e}$ between symptoms and symptom elements;

Step 3, based on the symptom combination feature representation H, determining a category of syndrome $y_s$ according to a formula:

$$y_s = \text{sigmoid}(W_2(W_1 * H + b_1) + b_2) \quad (12)$$

where $W_1$ and $W_2$ are the weight matrix of the first layer and the second layer, respectively, $b_1$ and $b_2$ are the offset vectors of the first layer and the second layer, respectively, and the category with the highest probability is the result of classification.

2. The TCM syndrome classification method based on multi-graph attention according to claim 1, wherein in Step 1, each clinical data is represented by multi-thermal coding of symptoms, syndrome elements and syndrome types: a symptom set $s=\{s_1, s_2, s_3, \ldots s_m\}$ a syndrome element set $se=\{se_1, se_2, se_3, \ldots se_k\}$ and a syndrome type set $sy=\{sy_1, sy_2, sy_3, \ldots sy_l\}$, where m is the number of symptoms contained in the data set, k is the number of syndrome elements contained in the data set, and l is the number of syndrome types contained in the data set; for any clinical data, if the i-th symptom/syndrome element/syndrome type appears, the corresponding position in the corresponding symptom set s/syndrome element set se/syndrome type set sy is set as 1, otherwise it is set as 0.

3. The TCM syndrome classification method based on multi-graph attention according to claim 1, wherein the specific step of constructing a symptom-symptom graph, a symptom-syndrome element graph and a symptom embedding matrix in Step 1 comprises:

Step 1-1: constructing a symptom-symptom undirected graph Ss: counting the frequency of all symptoms appearing in clinical data, extracting the symptoms with frequency ≥threshold M, and connecting the symptoms in pairs to form the symptom-symptom undirected graph Ss;

Step 1-2: constructing a symptom-syndrome element undirected graph Se: comparing any two clinical data, counting the number of the same syndrome elements in the two clinical data, and connecting the symptoms of the two clinical data if the number of the same syndrome elements is greater than the threshold N;

Step 1-3: constructing a symptom embedding matrix $em=\{em_1, em_2, em_3, \ldots em_n\}$, and defining $em_i=s=\{s_1, s_2, s_3, \ldots s_m\}$, where n is the total number of clinical data.

4. The TCM syndrome classification method based on multi-graph attention according to claim 1, wherein the formula of matrix splicing operation in Step 2 is as follows:

$$H_i = Cat(H_{i_s}, H_{i_e}) \quad (10)$$

where Cat is the splicing operation of two matrices.

5. The TCM syndrome classification method based on multi-graph attention according to claim 1, wherein the symptom combination feature representation H is as follows:

$$H = MUL(em, H_i) \quad (11)$$

where MUL is the multiplication operation of two matrices.

6. The TCM syndrome classification method based on multi-graph attention according to claim 1, $$y_s = \text{sigmoid}(W_2(W_1 * H + b_1) + b_2) \quad (12)$$

calculating difference L between the model prediction and the actual output used to train the model;

$$L = -\frac{1}{n}\sum_{s=1}^{n}[t_s\log(y_s) + (1-t_s)\log(1-y_s)] \qquad (13)$$

where n is the number of categories of the syndrome type, and $t_s$ is a real category.

7. The TCM syndrome classification method based on multi-graph attention according to claim 2, wherein the specific step of constructing a symptom-symptom graph, a symptom-syndrome element graph and a symptom embedding matrix in Step 1 comprises:

Step 1-1: constructing a symptom-symptom undirected graph Ss: counting the frequency of all symptoms appearing in clinical data, extracting the symptoms with frequency ≥threshold M, and connecting the symptoms in pairs to form the symptom-symptom undirected graph Ss;

Step 1-2: constructing a symptom-syndrome element undirected graph Se: comparing any two clinical data, counting the number of the same syndrome elements in the two clinical data, and connecting the symptoms of the two clinical data if the number of the same syndrome elements is greater than the threshold N;

Step 1-3: constructing a symptom embedding matrix em={$em_1$, $em_2$, $em_3$, ... $em_n$}, and defining $em_i$=s={$s_1$, $s_2$, $s_3$, ... $s_m$}, where n is the total number of clinical data.

\* \* \* \* \*